United States Patent [19]

Robertson et al.

[11] Patent Number: 4,758,574
[45] Date of Patent: Jul. 19, 1988

[54] 2-PHENYLIMIDAZIO (4,5-C) PYRIDINES

[75] Inventors: David W. Robertson; J. Scott Hayes, both of Indianapolis, Ind.

[73] Assignee: Eli Lilly and Company, Indianapolis, Ind.

[21] Appl. No.: 878,718

[22] Filed: Jun. 26, 1986

Related U.S. Application Data

[63] Continuation of Ser. No. 569,364, Jan. 9, 1984, abandoned, which is a continuation-in-part of Ser. No. 469,883, Feb. 25, 1983, abandoned, which is a continuation-in-part of Ser. No. 373,932, May 3, 1982, abandoned.

[51] Int. Cl.$^4$ ............................................. A61K 31/44
[52] U.S. Cl. ..................................... 514/303; 546/118
[58] Field of Search ....................... 546/118; 514/303

[56] References Cited

U.S. PATENT DOCUMENTS

| | | | |
|---|---|---|---|
| 3,985,891 | 10/1976 | Kutter et al. | 546/118 |
| 4,299,834 | 11/1981 | Austel et al. | 544/264 |
| 4,327,100 | 4/1982 | Austel et al. | 546/118 |
| 4,353,909 | 10/1982 | Diederen et al. | 546/118 |
| 4,575,505 | 3/1986 | Jonas et al. | 514/248 |
| 4,582,837 | 4/1986 | Hauel et al. | 546/118 |
| 4,603,139 | 7/1986 | King | 514/337 |
| 4,616,090 | 10/1986 | Jonas | 558/397 |

FOREIGN PATENT DOCUMENTS 820316  8/1969  Canada .

OTHER PUBLICATIONS

Drug of the Future, vol. VI, No. 7, 1981, p. 421.
Schramm, Nature vol. 303, Jun. 1983.
Derwent E/26 52573, abstracting German Patent DE No. 3,044,497.
Derwent E/37 76695, abstracting Belgian Patent No. 892,339.
U.S. patent application Ser. No. 453,565, filed Dec. 27, 1982, Docket No. X-5935, titled Inotropic Agents.
Ber., 71B, 2347 (1938, abstracted in CA 33:984(6).
J. Het. Chem., 17, 1757 (1980).
Mutation Research, 78, 323 (1980).
Org. Prep. Proced. Int., 12 (3-4), 234 (1980).
J. Med. Chem., 13 (4), 697 (1970).
J. Het. Chem., 6 (5), 605 (1966).
CA 96:68900f (1982), reporting Deposited Doc., 1980, VINITI 5441-80.
CA 63:5628F (1965), reporting Indian J. Chem., 3 (3), 138 (1965).
Derwent 06130 D/05.
J. Org. Chem., 29, 2403 (1964).
Derwent 09936 D/07.

Primary Examiner—Jane T. Fan
Attorney, Agent, or Firm—Robert A. Conrad; Leroy Whitaker

[57] ABSTRACT

This invention provides for certain 2-phenylimidazo[4,5-c]pyridines, their pharmaceutical formulations, and their use as positive inotropic agents, bronchodilators, vasodilators, and anticoagulants.

8 Claims, No Drawings

2-PHENYLIMIDAZIO (4,5-C) PYRIDINES

CROSS-REFERENCE

This application is a continuation of copending application Ser. No. 569,364, filed Jan. 9, 1984, now abandoned which is a continuation-in-part of application Ser. No. 469,883, filed Feb. 25, 1983, now abandoned, which is a continuation-in-part of application Ser. No. 373,932, filed May 3, 1982, now abandoned.

BACKGROUND OF THE INVENTION

The cardiac glycosides and the sympathomimetic amines are the principal inotropic agents used in the management of congestive heart failure. Although the cardiac glycosides, especially digitalis, are among the most frequently prescribed drugs, they have numerous liabilities such as a low therapeutic index and erratic absorption, and are associated with life-threatening arrhythmias and deleterious drug-drug interactions. In addition, many patients either do not respond, or become refractory to these agents. The sympathomimetic amines, such as dopamine and epinephrine, have limited utility due to positive chronotropic effects, arrhythmogenic properties, and oral ineffectiveness.

More recently, new classes of inotropic agents have been found. Among these, certain 2-phenylimidazo[4,5-b]pyridines (U.S. Pat. Nos. 3,985,891 and 4,327,100) have been shown to possess inotropic and anticoagulant activity. U.S. Pat. Nos. 4,299,834 and 4,353,909 describe similarly substituted purine and 6-hydroxy-imidazo[4,5-b]pyridine derivatives.

Weidenhagen and Weeden (*Ber.*, 71B, 2347 (1938); CA 33:984(6)) describe the preparation of 2-phenylimidazo[4,5-c]pyridine and the p-methoxyphenyl and p-aminophenyl analogs.

Middleton and Wibberly (*J. Het. Chem.*, 17, 1757 (1980)) describe the preparation of a variety of substituted imidazopyridines including o-hydroxy-, o-nitro-, m-chloro-, p-chloro-, p-nitro-, and p-amino-substituted 2-phenylimidazo[4,5-c]pyridines, and o-methyl-, o-chloro-, m-chloro-, m-nitro-, p-methyl-, p-bromo-, p-chloro-, p-nitro-, and m,m-dinitro-substituted 2-phenyl-4-chloroimidazo[4,5-c]pyridines. Some of these compounds were found to be active mutagens in the Ames test (Middleton, et al., *Mutation Research*, 78, 323 (1980)).

Both Lee, et al., *Org. Prep. Proced. Int.*, 12 (3-4), 234 (1980) and Haskell, et al., *J. Med. Chem.*, 13(4), 697 (1970) describe the preparation of 2-(2aminophenyl-)imidazo[4,5-c]pyridine.

Yutilov and Shcherbina, *Deposited Doc.*, 1980, VINITI 5441-80, reported in CA 96:68900f, have prepared 2-phenylimidazo[4,5-c]pyridines substituted in the phenyl ring with hydrogen, 4-methoxy, 4-dimethylamino, 4,3- and 2,3-hydroxy-methoxy, and 3,4- and 2,5-dimethoxy.

The preparation of 2-(2-hydroxyphenyl)imidazo[4,5-c]pyridine was reported by Spector and Joullie' in *J. Het. Chem.*, 6(5), 605 (1966).

The present invention provides for a series of 2-phenylimidazo[4,5-c]pyridines, their formulations, and their use as orally effective positive inotropic agents which have minimal effects on blood pressure and heart rate. The compounds also possess vasodilitation, bronchodilation, and anticoagulant activities.

SUMMARY OF THE INVENTION

This invention provides for pharmaceutically useful imidazopyridine compounds having the formula

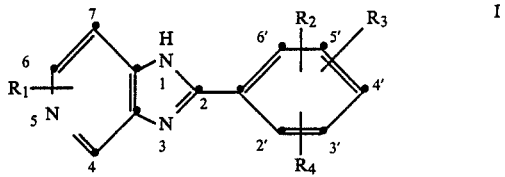

and

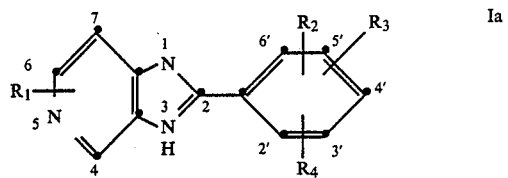

and their pharmaceutically acceptable salts, wherein $R_1$ is hydrogen, $C_1$–$C_4$ alkyl, or chloro;

$R_2$ and $R_3$ each are independently hydrogen, $C_1$–$C_4$ alkyl, $C_1$–$C_4$ alkoxy, allyloxy, $C_1$–$C_4$ alkylthio, $C_1$–$C_4$ alkylsulfinyl, $C_1$–$C_4$ alkylsulfonyl, hydroxy, halo, cyano, nitro, amino, mono- or di-($C_1$–$C_4$ alkyl)amino, trifluoromethyl, or Z-Q-substituted $C_1$–$C_4$ alkoxy, wherein Q is oxygen, sulfur, sulfinyl, sulfonyl, or a bond, and Z is $C_1$–$C_4$ alkyl, phenyl, or phenyl substituted with halo, $C_1$–$C_4$ alkyl, $C_1$–$C_4$ alkoxy, hydroxy, nitro, amino, $C_1$–$C_4$ alkylthio, $C_1$–$C_4$ alkylsulfinyl, or $C_1$–$C_4$ alkylsulfonyl; and $R_4$ is hydrogen, $C_1$–$C_4$ alkyl, or $C_1$–$C_4$ alkoxy;

with the provisions that:

(a) if $R_1$ and two of $R_2$, $R_3$, and $R_4$ are all hydrogen, the other of $R_2$, $R_3$, and $R_4$ is not hydrogen, halo, hydroxy, nitro, amino, di-($C_1$–$C_2$ alkyl)amino, or $C_1$–$C_2$ alkoxy;

(b) if $R_1$ and one of $R_2$, $R_3$, and $R_4$ are both hydrogen, and another of $R_2$, $R_3$, and $R_4$ is $C_1$–$C_2$ alkoxy, the other of $R_2$, $R_3$, and $R_4$ is not hydroxy or $C_1$–$C_2$ alkoxy;

(c) if $R_1$ is chloro and two of $R_2$, $R_3$, and $R_4$ are both hydrogen, the other of $R_2$, $R_3$, and $R_4$ is not hydrogen, halo, $C_1$–$C_2$ alkyl, or nitro; and (d) if $R_1$ is chloro and $R_4$ is hydrogen, $R_2$ and $R_3$ may not both be nitro.

In addition to the compounds of formula I and Ia, this invention also provides a method of treating a mammal, including a human, suffering from or susceptible to the conditions of asthma, thrombosis, hypertension, or heart failure, which comprises administering to said mammal a therapeutically effective amount of a compound of formula

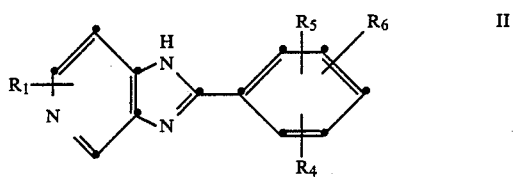

or

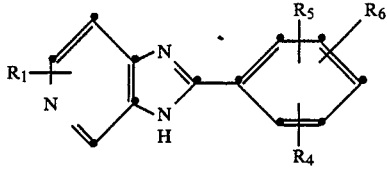

and their pharmaceutically acceptable salts, wherein
$R_1$ is hydrogen, $C_1-C_4$ alkyl, or chloro;
$R_4$ is hydrogen, $C_1-C_4$ alkyl, or $C_1-C_4$ alkoxy;
each of $R_5$ and $R_6$ is independently hydrogen, $C_1-C_4$ alkyl, $C_1-C_4$ alkoxy, allyloxy, $C_1-C_4$ alkylthio, $C_1-C_4$ alkylsulfinyl, $C_1-C_4$ alkylsulfonyl, hydroxy, halo, cyano, nitro, amino, mono- or di-($C_1-C_4$ alkyl)amino, trifluoromethyl, or Z-Q-substituted $C_1-C_4$ alkoxy, wherein Q is oxygen, sulfur, sulfinyl, sulfonyl, or a bond, and Z is $C_1-C_4$ alkyl, phenyl, or phenyl substituted with halo, $C_1-C_4$ alkyl, $C_1-C_4$ alkoxy, hydroxy, nitro, amino, $C_1-C_4$ alkylthio, $C_1-C_4$ alkylsulfinyl, or $C_1-C_4$ alkylsulfonyl.

According to a further aspect of the present invention there is provided a pharmaceutical formulation which comprises as active ingredient a compound of Formula II or IIa as defined above associated with a pharmaceutically acceptable carrier therefor.

DETAILED DESCRIPTION AND PREFERRED EMBODIMENT

The Formulae I and Ia, and II and IIa are recognized as being tautomeric structures of one another. The imidazopyridines having the hydrogen atom on the N-1 nitrogen atom and having the pyridine nitrogen atom at the 5-position (Formulas I and II, properly named 2-phenyl-1H-imidazo[4,5-c]pyridines) have corresponding tautomeric forms wherein the hydrogen atom is on the N-3 nitrogen atom (Formulas Ia and IIa, 2-phenyl-3H-imidazo[4,5-c]pyridines). As N-unsubstituted compounds, each tautomeric form exists in equilibrium with the other and cannot be prepared or isolated without the presence of the other. For this application, both forms will be considered together and will be referred to as 2-phenyl-1(3)H-imidazo[4,5-c]pyridines, 2-phenyl-imidazo[4,5-c]pyridines, or compounds of Formula I (Ia) and II (IIa).

A preferred group of compounds for treating mammals are the compounds of Formula II (IIa) wherein
$R_1$ and $R_4$ are each hydrogen;
each of $R_5$ and $R_6$ is independently hydrogen, $C_1-C_4$ alkyl, $C_1-C_4$ alkoxy, halogen, trifluoromethyl, $C_1-C_4$ alkylthio, $C_1-C_4$ alkylsulfinyl, $C_1-C_4$ alkylsulfonyl, or Z-Q-substituted $C_1-C_4$ alkoxy; and pharmaceutically acceptable salts thereof.

Preferred groups of compounds are those compounds wherein $R_5$ and $R_6$ are substituted at the 3'- and 4'-positions, or especially the 2'- and 4'-positions of the phenyl ring.

Especially preferred compounds as defined above are those where "$C_1-C_4$ alkyl" is methyl, "$C_1-C_4$ alkylsulfinyl" is methylsulfinyl, "$C_1-C_4$ alkylsulfonyl" is methylsulfonyl, and "$C_1-C_4$ alkoxy" is methoxy. Preferred Z-Q-substituted $C_1-C_4$ alkoxy compounds are those wherein $C_1-C_4$ alkoxy is ethoxy or n-propoxy, Q is oxygen, sulfur, sulfinyl, or sulfonyl, and Z is $C_1-C_4$ alkyl, phenyl, or phenyl substituted with halo, $C_1-C_4$ alkoxy, or hydroxy. Compounds substituted at the 2'-position of the phenyl ring with $C_1-C_4$ alkoxy, especially methoxy, or with the preferred Z-Q-substituted $C_1-C_4$ alkoxy substituents, and at the 4'-position of the phenyl ring with trifluoromethyl, $C_1-C_4$ alkoxy, $C_1-C_4$ alkylsulfinyl, or $C_1-C_4$ alkylsulfonyl are particularly preferred, with 2-(2,4-dimethoxyphenyl)imidazo[4,5-c]pyridine, 2-(2-methoxy-4-methylsulfinylphenyl)imidazo[4,5-c]pyridine, 2-(2-methoxy-4-methylsulfonylphenyl)imidazo[4,5-c]pyridine, and 2-(2-methoxy-4-trifluoromethylphenyl)imidazo[4,5-c]pyridine being the most preferred compounds.

In addition to the inotropic and other activities possessed by the compounds of this invention, we have discovered that certain of the compounds of Formula II (IIa) lower blood pressure but do not cause the expected reflex tachycardia, i.e., they appear to possess bradycardic activity. This pharmacological profile can be desirable for a compound used in the treatment of hypertension or heart failure. These compounds are those generally defined as compounds of Formula II (IIa) wherein $R_1$ and $R_4$ are both hydrogen, $R_5$ is Z-Q-substituted $C_1-C_4$ alkoxy at the 2'-position of the phenyl ring, and $R_6$ is $C_1-C_4$ alkoxy, $C_1-C_4$ alkylthio, $C_1-C_4$ alkylsulfinyl, or $C_1-C_4$ alkylsulfonyl at the 4'-position. The preferred compounds are those containing the preferred functionalities as previously defined.

The following definitions refer to the various terms used throughout this disclosure.

The term "halo" refers to fluoro, chloro, bromo, and iodo.

The term "$C_1-C_4$ alkyl" refers to the straight and branched aliphatic radicals of one to four carbon atoms including methyl, ethyl, propyl, isopropyl, butyl, isobutyl, sec-butyl, and tert-butyl. The term "$C_1-C_2$ alkyl" refers to methyl and ethyl.

The term "$C_1-C_4$ alkoxy" includes the straight and branched aliphatic ether radicals of one to four carbon atoms such as methoxy, ethoxy, propoxy, isopropoxy, butoxy, isobutoxy, sec-butoxy, and tertbutoxy. The term "$C_1-C_2$ alkoxy" refers to methoxy and ethoxy.

The compounds of this invention as represented by Formulas II and IIa may be prepared by any of several methods known in the art.

A preferred method of preparation consists of the reaction of a pyridine of the formula

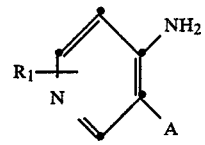

wherein A is amino and $R_1$ is as defined above, with a compound of the formula

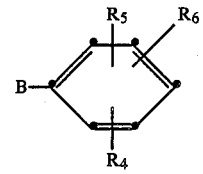

wherein B is —COOH, and $R_4$, $R_5$, $R_6$ are as defined above. The reaction may be performed in the absence of a solvent, but is generally carried out in a suitable non-reactive solvent, such as benzene, toluene, xylene, ethylene glycol, pyridine, acetone, phosphorous oxychloride, polyphosphoric acid, and the like, optionally in the presence of a base, such as pyridine or triethylamine, or optionally in the presence of a catalytic amount of an acid, such as p-toluenesulfonic acid, or optionally in the presence of a dehydrating agent, such as phosphorous oxychloride, phosphorous pentoxide, or thionyl chloride. Temperatures in the range of −20° C. to 250° C. may be employed with a preferred range of 50°–200° C.

Other similar methods of preparing the compounds are likewise known. Carboxylic acid derivatives IV may be employed in the above sequence with appropriate modifications in the reaction conditions. For example, an amide derivative of IV may be substituted for the benzoic acid when condensing with the diaminopyridine III, preferably in the presence of a dehydrating agent or base at elevated temperatures, especially in the temperature range of 100°–150° C. If B of Formula IV is cyano, the reaction with the pyridinediamine is typically performed in the presence of a catalytic quantity of an acid, such as p-toluenesulfonic acid, usually at temperatures of 120°–180° C. If B is a thioamide derivative, the condensation with the diaminopyridine is best effected in a solvent, such as ethylene glycol, at temperatures of 100°–150° C. If, in Formula III, A is a halogen, the reaction is performed with the respective amidine derivative of IV. The intermediate thus formed may be first isolated or generated in situ, followed by cyclization at elevated temperatures, preferably in the range of 100°–200° C.

In the preferred scheme above, when the benzoic acid IV (B is —COOH) is unsubstituted or is substituted with unreactive functionalities (e.g., alkyl, halogen, etc.), heating with the diaminopyridine in polyphosphoric acid (PPA) is the most convenient and preferred method of preparing the respective imidazopyridine. This method was described by Middleton and Wibberley, *J. Het. Chem.*, 17, 1757 (1980), for the preparation of imidazo[4,5-b]- and [4,5-c]pyridines.

When the benzoic acids of Formula IV are substituted with groups such as alkoxy, PPA treatment can lead to dealkylation and the preferred conditions for the reaction are by refluxing the reactants in phosphorous oxychloride or xylene with the azeotropic removal of water.

Especially when the benzoic acids (IV) contain phenolic or amino substituents, an alternate method of preparation may be employed. A substituted benzaldehyde (IV, B is —CHO) may be treated with sulfur and morpholine to produce the respective substituted-thiobenzoic acid morpholide which on further treatment with methyl iodide gives the S-methyl-substituted-thiobenzoic acid morpholide iodide derivative. Treatment of this intermediate with the appropriate diaminopyridine (III, A is amino) in a solvent such as ethylene glycol with heating produces the desired product II (IIa). By this scheme, 2-methoxybenzaldehyde was converted first to 2-methoxy-thiobenzoic acid morpholide, then to S-methyl-2-methoxy-thiobenzoic acid morpholide iodide, which on heating in ethylene glycol with 3,4-diaminopyridine gave II (IIa) ($R_1$, $R_5$, and $R_6$ are each hydrogen; $R_4$ is 2′-methoxy).

The starting material 3,4-diaminopyridine is commercially available. Other required pyridines of Formula III are either commercially available, or may be prepared in the usual manner from available starting materials by the proper sequence of nitrations, reductions, acylations, hydrolyses, halogenations, and aminations. The required benzoic acids and derivatives of Formula IV are either commercially available, are known in the literature, or are prepared by methods known in the art.

In addition, some of the compounds of Formula II (IIa) may be prepared by subsequent derivatizations of other compounds of Formula II (IIa) by methods known in the art. Thus, amine derivatives may be prepared from intermediate halo derivatives, phenol substituents may be selectively alkylated, and the like. The sulfinyl and sulfonyl derivatives of this invention may be prepared directly by the reaction of the corresponding intermediates III with IV, or by oxidation of the corresponding mercapto compounds of Formula II (IIa) by methods known in the art. One or two equivalents, respectively, of hydrogen peroxide in an alcohol, a peracid, such as meta-chloroperbenzoic acid in methylene chloride, or similar oxidants may be used to effect these transformations.

Illustrative of the compounds of this invention are the following:

2-[2-($\beta$-methylsulfinylethoxy)-4-methoxyphenyl]imidazo[4,5-c]pyridine, 2-(2-methoxy-5-methylsulfonylphenyl)imidazo[4,5-c]pyridine, 2-[2-methoxy-4-($\gamma$-methylmercaptopropoxy)phenyl]imidazo[4,5-c]pyridine, 2-[2-methoxy-4-($\beta$-ethylsulfinylethoxy)phenyl]imidazo[4,5-c]pyridine, 2-(2-butoxy-4-methylphenyl)imidazo[4,5-c]pyridine, 2-[2-($\gamma$-methylsulfinylpropoxy)-4-methoxyphenyl]imidazo[4,5-c]pyridine, 2-[2-($\beta$-methylsulfinylethoxy)-4-chlorophenyl]imidazo[4,5-c]pyridine, 2-(2-methoxy-4-methylphenyl)imidazo[4,5-c]pyridine, 2-(2-methoxy-4-methylsulfinylphenyl)imidazo[4,5-c]pyridine, 2-[2-($\beta$-methylmercaptoethoxy)-5-methylmercaptophenyl]imidazo[4,5-c]pyridine, 2-[2-($\beta$-ethylsulfinylethoxy)-4-methoxyphenyl]imidazo[4,5-c]pyridine, 2-(2-methoxy-4-hydroxyphenyl)imidazo[4,5-c]pyridine, 2-(2,4-dimethoxyphenyl)-7-methyl-imidazo[4,5-c]pyridine, 2-(2,3-dimethoxyphenyl)imidazo[4,5-c]pyridine, 2-(2,4,5-trimethoxyphenyl)imidazo[4,5-c]pyridine, 2-[2-($\beta$-methylsulfinylethoxy)-4-methylphenyl]imidazo[4,5-c]pyridine, 2-[2-methoxy-4-($\beta$-methylmercaptoethoxy)phenyl]imidazo[4,5-c]pyridine, 2-(2,5-dimethoxyphenyl)imidazo[4,5-c]pyridine, 2-(2-fluoro-5-methylsulfinylphenyl)imidazo[4,5-c]pyridine, 2-(2,4-dimethoxyphenyl)-6-methyl-imidazo[4,5-c]pyridine, 2-(2-ethoxy-4-propylsulfinylphenyl)imidazo[4,5-c]pyridine, 2-[2-($\beta$-methoxyethoxy)-4-methoxyphenyl]imidazo[4,5-c]pyridine, 2-(2-ethoxy-4-ethylsulfonylphenyl)imidazo[4,5-c]pyridine, 2-(4-isopropoxyphenyl)-7-butyl-imidazo[4,5-c]pyridine, 2-(2-$\beta$-phenylsulfinylethoxy-4-methoxyphenyl)imidazo[4,5-c]pyridine, 2-[2-($\beta$-methylmercaptoethoxy)-4-methylmercaptophenyl]imidazo[4,5-c]pyridine, 2-(2-methylmercaptophenyl)imidazo[4,5-c]pyridine, 2-[2,4-bis(methylmercapto)phenyl]imidazo[4,5-c]pyridine, 2-(2,4-diethoxyphenyl)imidazo[4,5-c]pyridine, 2-[2-(β-ethylmercaptoethoxy)-4-methoxyphenyl-]imidazo[4,5-c]pyridine,
2-(2-methoxy-4-propylsulfonylphenyl)imidazo[4,5-c]pyridine,
2-(2-ethoxy-5-methylsulfinylphenyl)imidazo[4,5-c]pyridine,
2-(4-aminophenyl)imidazo[4,5-c]pyridine,
2-(2,4-dimethoxyphenyl)imidazo[4,5-c]pyridine,
2-(2-ethoxy-4-ethylsulfinylphenyl)imidazo[4,5-c]pyridine,
2-(2,4,6-trimethoxyphenyl)imidazo[4,5-c]pyridine,
2-(2-ethoxy-4-butylsulfinylphenyl)imidazo[4,5-c]pyridine,
2-(2-methoxy-5-methylsulfinylphenyl)imidazo[4,5-c]pyridine,
2-(3-methoxy-4-hydroxyphenyl)imidazo[4,5-c]pyridine,
2-(2,6-dichlorophenyl)imidazo[4,5-c]pyridine,
2-(2-ethoxy-4-butylsulfonylphenyl)imidazo[4,5-c]pyridine,
2-[2-β-(4-hydroxyphenylsulfinyl)ethoxy-4methoxyphenyl]imidazo[4,5-c]pyridine,
2-(2-fluoro-4-methoxyphenyl)imidazo[4,5-c]pyridine,
2-(2-methylaminophenyl)imidazo[4,5-c]pyridine,
2-(4-methylmercaptophenyl)imidazo[4,5-c]pyridine,
2-(2-allyloxy-4-methoxyphenyl)imidazo[4,5-c]pyridine,
2-[2-methoxy-4-(β-ethylmercaptoethoxy)phenyl-]imidazo[4,5-c]pyridine,
2-(2,4-dimethoxyphenyl)-6-chloro-imidazo[4,5-c]pyridine,
2-(2-methoxyphenyl)-7-butyl-imidazo[4,5-c]pyridine,
2-(2-fluoro-4-methylsulfinylphenyl)imidazo[4,5-c]pyridine,
2-(3-butyl-4-methoxyphenyl)imidazo[4,5-c]pyridine,
2-(3,4-dimethoxyphenyl)imidazo[4,5-c]pyridine,
2-(2-chlorophenyl)imidazo[4,5-c]pyridine,
2-(2-ethoxy-4-butylmercaptophenyl)imidazo[4,5-c]pyridine,
2-(2-fluoro-5-methylmercaptophenyl)imidazo[4,5-c]pyridine,
2-(4-hydroxyphenyl)imidazo[4,5-c]pyridine,
2-(2-ethoxy-4-methylphenyl)imidazo[4,5-c]pyridine,
2-(4-methoxyphenyl)imidazo[4,5-c]pyridine,
2-[2-methoxy-4-(β-methylsulfinylethoxy)phenyl-]imidazo[4,5-c]pyridine,
2-[2-γ-(3,4-dichlorophenoxy)propoxyphenyl-]imidazo[4,5-c]pyridine,
2-[2-(β-methylsulfinylethoxy)-4-methylmercaptophenyl]imidazo[4,5-c]pyridine,
2-(2,4-dimethoxy-3-hydroxyphenyl)imidazo[4,5-c]pyridine,
2-(2-hydroxy-4-methoxyphenyl)imidazo[4,5-c]pyridine,
2-(2-ethoxy-4-propylmercaptophenyl)imidazo[4,5-c]pyridine,
2-(2-fluoro-5-methylsulfonylphenyl)imidazo[4,5-c]pyridine,
2-(2-methoxy-4-butylmercaptophenyl)imidazo[4,5-c]pyridine,
2-[2-(γ-ethylsulfinylpropoxy)-4-methoxyphenyl-]imidazo[4,5-c]pyridine,
2-[2-(β-methylsulfinylethoxy)-4-methylsulfinylphenyl]imidazo[4,5-c]pyridine,
2-(2-methoxy-4-propylsulfinylphenyl)imidazo[4,5-c]pyridine,
2-(3,5-dimethoxyphenyl)imidazo[4,5-c]pyridine,
2-[2-(β-methylmercaptoethoxy)-4-methoxyphenyl-]imidazo[4,5-c]pyridine,
2-(2,6-dimethoxyphenyl)imidazo[4,5-c]pyridine,
2-(2-methoxy-4-ethoxyphenyl)imidazo[4,5-c]pyridine,
2-(2-methoxy-4-dimethylaminophenyl)imidazo[4,5-c]pyridine,
2-(4-nitro-2-hydroxyphenyl)imidazo[4,5-c]pyridine,
2-(3-cyanophenyl)imidazo[4,5-c]pyridine,
2-(4-isqpropylphenyl)imidazo[4,5-c]pyridine,
2-(2-β-phenylethoxyphenyl)imidazo[4,5-c]pyridine,
2-(2,4-dimethoxyphenyl)-6-ethyl-imidazo[4,5-c]pyridine,
2-(2,4-dihydroxyphenyl)imidazo[4,5-c]pyridine,
2-(2-methoxy-4-methylsulfonylphenyl)imidazo[4,5-c]pyridine,
2-(2-methoxy-4-propylmercaptophenyl)imidazo[4,5-c]pyridine,
2-[2-methoxy-4-(γ-ethylsulfinylpropoxy)phenyl-]imidazo[4,5-c]pyridine,
2-(2-methoxy-4-chlorophenyl)imidazo[4,5-c]pyridine,
2-[2-(γ-ethylmercaptopropoxy)-4-methoxyphenyl-]imidazo[4,5-c]pyridine,
2-(4-methylsulfonylphenyl)imidazo[4,5-c]pyridine,
2-(2-hexyloxy-4-methylphenyl)imidazo[4,5-c]pyridine,
2-(2-octyloxy-4-methoxyphenyl)imidazo[4,5-c]pyridine,
2-(2-methoxy-4-ethylmercaptophenyl)imidazo[4,5-c]pyridine,
2-(4-dimethylaminophenyl)imidazo[4,5-c]pyridine,
2-[2-methoxy-4-(γ-ethylmercaptopropoxy)phenyl-]imidazo[4,5-c]pyridine,
2-(2,4-dimethylphenyl)imidazo[4,5-c]pyridine,
2-(2-methylsulfinylphenyl)imidazo[4,5-c]pyridine,
2-[2-(β-n-butylsulfinylethoxy)-5-methylmercaptophenyl]imidazo[4,5-c]pyridine,
2-(2,4-dimethoxyphenyl)-5-methyl-imidazo[4,5-c]pyridine,
2-(2-methoxy-4-methylmercaptophenyl)imidazo[4,5-c]pyridine,
2-(2,3,4-trimethoxyphenyl)imidazo[4,5-c]pyridine,
2-(3,4,5-trimethoxyphenyl)imidazo[4,5-c]pyridine,
2-(2-methoxy-4-ethylsulfinylphenyl)imidazo[4,5-c]pyridine,
2-[2-(β-methylsulfinylethoxy)phenyl]imidazo[4,5-c]pyridine,
2-[2-(δ-methylmercaptobutoxy)-4-methoxyphenyl-]imidazo[4,5-c]pyridine,
2-(4-iodophenyl)-6-chloro-imidazo[4,5-c]pyridine,
2-[2-methoxy-4-(β-butylsulfinylethoxy)phenyl-]imidazo[4,5-c]pyridine,
2-[2-(β-methoxyethoxy)phenyl]imidazo[4,5-c]pyridine,
2-(2-fluorophenyl)imidazo[4,5-c]pyridine,
2-(3-isopropoxyphenyl)imidazo[4,5-c]pyridine,
2-(2-ethoxy-4-ethylmercaptophenyl)imidazo[4,5-c]pyridine,
2-(4-fluoro-2-methoxyphenyl)imidazo[4,5-c]pyridine,
2-(2-methoxy-5-methylmercaptophenyl)imidazo[4,5-c]pyridine,
2-(2-fluoro-4-methylmercaptophenyl)imidazo[4,5-c]pyridine,
2-[2-methoxy-4-(γ-methylsulfinylpropoxy)phenyl-]imidazo[4,5-c]pyridine,
2-(2-methylsulfonylphenyl)imidazo[4,5-c]pyridine,
2-(4-butoxyphenyl)imidazo[4,5-c]pyridine,
2-(4-methylsulfinylphenyl)imidazo[4,5-c]pyridine, and
2-(2-methoxy-4-benzyloxyphenyl)imidazo[4,5-c]pyridine.

The pharmaceutically acceptable acid addition salts of this invention include salts derived from inorganic acids such as hydrochloric acid, nitric acid, phosphoric acid, sulfuric acid, hydrobromic acid, hydriodic acid, phosphorous acid and the like, as well as salts derived from nontoxic organic acids such as aliphatic mono and dicarboxylic acids, phenyl-substituted alkanoic acids, hydroxy alkanoic and alkandioic acids, aromatic acids, aliphatic and aromatic sulfonic acids, etc. Such pharmaceutically acceptable salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, fluoride, acetate, propionate, decanoate, caprylate, acrylate, formate, isobutyrate, caprate, heptanoate, propiolate, oxalate, malonate, succinate, suberate, sebacate, fumarate, maleate, mandelate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, $\beta$-hydroxybutyrate, glycolate, malate, tartrate, methanesulfonate, propanesulfonate, naphthalene-1-sulfonate, naphthalene-2-sulfonate and the like salts. The preferred salts of this invention are those derived from inorganic acids, especially hydrochloric acid.

The compounds may be administered by various routes including the oral, rectal, transdermal, subcutaneous, intravenous, intramuscular, or intranasal routes, being usually employed in the form of a pharmaceutical composition. It is a special feature of these compounds that they are effective positive inotropic agents, vasodilators, or bronchodilators following oral administration. Such compositions are prepared in a manner well known in the pharmaceutical art and comprise at least one active compound. Accordingly, the invention includes a pharmaceutical composition comprising as active ingredient a compound of Formula II (IIa) or an acid addition salt thereof associated with a pharmaceutically acceptable carrier.

In making the compositions of the present invention, the active ingredient will usually be mixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the composition can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions and sterile packaged powders.

Some examples of suitable carriers are lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, methyl cellulose, methyl- and propyl-hydroxybenzoates, talc, magnesium stearate or mineral oil. The formulations can additionally include lubricating agents, wetting agents, emulsifying and suspending agents, preserving agents, sweetening agents or flavoring agents. The compositions of the invention may, as is well known in the art, be formulated so as to provide quick, sustained or delayed release of the active ingredient after administration to the patient.

The compositions are preferably formulated in a unit dosage form, each dosage containing from about 5 to 500 mg., more usually about 25 to 300 mg., of the active ingredient. The term "unit dosage form" refers to physically discrete units suitable as unitary dosages for human subjects and other mammals, each unit containing a predetermined quantity of active material calculated to produce the desired therapeutic effect, in association with the required pharmaceutical carrier.

The active compounds are effective over a wide dosage range. For example, dosages per day will normally fall within the range of about 0.5 to 300 mg./kg. In the treatment of adult humans, the range of about 1 to 50 mg./kg., in single or divided doses, is preferred. However, it will be understood that the amount of the compound actually administered will be determined by a physician, in the light of the relevant circumstances including the condition to be treated, the choice of compound to be administered, the chosen route of administration, the age, weight, and response of the individual patient, and the severity of the patient's symptoms, and therefore the above dosage ranges are not intended to limit the scope of the invention in any way.

The following examples further illustrate the preparation of the compounds and formulations of this invention.

EXAMPLE 1

2-(3-Fluorophenyl)imidazo[4,5-c]pyridine hydrochloride

A mixture of 3,4-diaminopyridine (1.09 g., 1 mmoles), 3-fluorobenzoic acid (1.40 g., 10 mmoles), and polyphosphoric acid (PPA, 40 g.) was heated to about 200° C. with stirring for 3.5 hours. The solution was then slowly added to water. The solution was then neutralized by the addition of 50% aqueous sodium hydroxide and the resulting precipitate was collected by filtration. Crystallization from isopropanol/water gave 1.72 g. (81% yield) of 2-(3-fluorophenyl)imidazo[4,5-c]pyridine (base), m.p. about 290°–291° C.

Analysis: $C_{12}H_8FN_3$; Calc: C, 67.60; H, 3.78; N, 19.71; F, 8.91; Found: C, 67.44; H, 3.97; N, 19.51; F, 8.63.

The title hydrochloride salt was prepared from the above base by treating with ethanolic hydrogen chloride and crystallizing from ethanol/water, m.p. about 269°–272° C.

Analysis: $C_{12}H_9ClFN_3$; Calc: C, 57.73; H, 3.63; N, 16.83; F, 7.61; Cl, 14.20; Found: C, 57.50; H, 3.85; N, 16.57; F, 7.80; Cl, 13.98.

EXAMPLE 2

2-(3-Methylphenyl)imidazo[4,5-c]pyridine

The title compound was prepared in 70% yield according to the procedure in Example 1 using 3-methylbenzoic acid and 3,4-diaminopyridine. Crystallization from methanol/water afforded light tan crystals, m.p. about 202.5°–204° C.

Analysis: $C_{13}H_{11}N_3$; Calc: C, 74.62; H, 5.30; N, 20.08; Found: C, 74.39; H, 5.00; N, 19.88.

EXAMPLE 3

2-(3,5-Dichlorophenyl)imidazo[4,5-c]pyridine hydrochloride

When 3,5-dichlorobenzoic acid and 3,4-diaminopyridine were reacted according to the procedure in Example 1, the title compound (base) was obtained. Upon converting to the hydrochloride salt and crystallization from ethanol/dimethylformamide/water, a 61% yield of pure 2-(3,5-dichlorophenyl)imidazo[4,5-c]pyridine hydrochloride was obtained as cream-colored needles, m.p. >320° C.

Analysis: $C_{12}H_8Cl_3N_3$; Calc: C, 47.95; H, 2.68; N, 13.98; Cl, 35.39; Found: C, 47.71; H, 2.51; N, 13.78; Cl, 35.37.

EXAMPLE 4

2-(4-Methylsulfonylphenyl)imidazo[4,5-c]pyridine hydrochloride

Following the procedure of Example 1, the reaction of 4-methylsulfonylbenzoic acid and 3,4-diaminopyridine gave the title compound as the free base. On conversion to the hydrochloride salt and crystallization from methanol/water, the desired product was obtained as small flocculent needles, m.p. >320° C.

Analysis: $C_{13}H_{12}ClN_3O_2S$; Calc: C, 50.41; H, 3.90; N, 13.57; S, 10.35; Cl, 11.44; O, 10.33; Found: C, 50.41; H, 4.02; N, 13.33; S, 10.20; Cl, 11.24; O, 10.21.

EXAMPLE 5

2-(4-Fluorophenyl)imidazo[4,5-c]pyridine hydrochloride

The free base of the title compound was prepared following the procedure of Example 1 using 4-fluorobenzoic acid and 3,4-diaminopyridine. The hydrochloride salt was obtained as a light tan solid, m.p. about 320° C. (decomposes).

Analysis: $C_{12}H_9ClFN_3$; Calc: C, 57.73; H, 3.63; N, 16.83; Found: C, 57.94; H, 3.87; N, 16.42.

EXAMPLE 6

2-(2-Fluorophenyl)imidazo[4,5-c]pyridine hydrochloride

The title compound was obtained as a light green solid when the free base, made from 2-fluorobenzoic acid and 3,4-diaminopyridine according to Example 1, was converted to the hydrochloride salt, m.p. about 243°–245° C.

Analysis: $C_{12}H_9ClFN_3$; Calc: C, 57.04; H, 3.63; N, 16.83; Found: C, 56.65; H, 3.54; N, 16.67.

EXAMPLE 7

2-Phenylimidazo[4,5-c]pyridine

The title compound was prepared according to the procedure of Middleton and Wibberly, *J. Het. Chem.*, 17, 1757 (1980), m.p. about 225°–226° C.

Analysis: $C_{12}H_9N_3$; Calc: C, 73.83; H, 4.65; N, 21.52; Found: C, 73.72; H, 4.85; N, 21.61.

EXAMPLE 8

2-(2,4-Dimethoxyphenyl)imidazo[4,5-c]pyridine hydrochloride

A mixture of 3,4-diaminopyridine (10.90 g., 100 mmoles) and 2,4-dimethoxybenzoic acid (18.20 g., 100 mmoles) was added to 400 ml. of phosphorous oxychloride and the resulting mixture was heated to reflux for about 4 hours. After cooling, the excess phosphorous oxychloride was removed under reduced pressure and the residue was treated with 200 ml. of 1N hydrochloric acid. The resulting solution was neutralized with 50% aqueous sodium hydroxide and the precipitated product was collected by filtration. Flash chromatography over silica gel (methylene chloride/methanol, 15:1) and recrystallization from ethanol/water saturated with hydrogen chloride gave the title product (16.54 g., 57% yield) as light tan needles, m.p. about 231°–234° C.

Analysis: $C_{14}H_{14}ClN_3O_2$; Calc: C, 57.64; H, 4.84; N, 14.40; Cl, 12.15; Found: C, 57.59; H, 5.04; N, 14.17; Cl, 11.82.

EXAMPLES 9–23

Following the procedure of Example 8, the following compounds were prepared using the appropriate benzoic acid and 3,4-diaminopyridine:

9. 2-(4-methylmercaptophenyl)imidazo[4,5-c]pyridine hydrochloride, yellow crystals, m.p. about 307°–309° C.

Analysis: $C_{13}H_{12}ClN_3S$; Calc: C, 56.21; H, 4.35; N, 15.13; S, 11.54; Cl, 12.76; Found: C, 55.97; H, 4.16; N, 14.90; S, 11.37; Cl, 12.78.

10. 2-(3,4,5-trimethoxyphenyl)imidazo[4,5-c]pyridine hydrochloride, light yellow crystals, m.p. about 248°–250° C.

Analysis: $C_{15}H_{16}ClN_3O_3$; Calc: C, 55.99; H, 5.01; N, 13.06; Cl, 11.02; Found: C, 55.73; H, 5.19; N, 12.97; Cl, 10.77.

11. 2-(2,3-dimethoxyphenyl)imidazo[4,5-c]pyridine hydrochloride, light yellow crystals, m.p. about 279°–281° C.

Analysis: $C_{14}H_{14}ClN_3O_2$; Calc: C, 57.64; H, 4.84; N, 14.40; Cl, 12.15; Found: C, 57.40; H, 4.90; N, 14.25; Cl, 12.04.

12. 2-(3-nitrophenyl)imidazo[4,5-c]pyridine hydrochloride, white crystals, m.p. about 265° C. (decomposition).

Analysis: $C_{12}H_9ClN_4O_2$; Calc: C, 52.09; H, 3.28; N, 20.25; Found: C, 52.31; H, 3.37; N, 19.98.

13. 2-(4-ethoxyphenyl)imidazo[4,5-c]pyridine hydrochloride, light tan solid, m.p. about 284°–286° C.

Analysis: $C_{14}H_{14}ClN_3O$; Calc: C, 59.66; H, 4.62; N, 16.06; Found: C, 60.01; H, 4.75; N, 15.84.

14. 2-(4-cyanophenyl)imidazo[4,5-c]pyridine hydrochloride, yellow solid, m.p. >320° C.

Analysis: $C_{13}H_9ClN_4$; Calc: C, 60.83; H, 3.53; N, 21.83; Found: C, 60.56; H, 3.71; N, 21.64.

15. 2-(4-methoxyphenyl)imidazo[4,5-c]pyridine hydrochloride, light tan needles, m.p. about 271°–273° C.

Analysis $C_{13}H_{12}ClN_3O$; Calc: C, 59.66; H, 4.62; N, 16.06; Cl, 13.55; Found: C, 59.85; H, 4.45; N, 15.97; Cl, 13.11.

16. 2-(3-methoxyphenyl)imidazo[4,5-c]pyridine hydrochloride, light tan solid, m.p. about 258°–260° C.

Analysis: $C_{13}H_{12}ClN_3O$; Calc: C, 59.66; H, 4.62; N, 16.06; Cl, 13.55; Found: C, 59.39; H, 4.72; N, 15.80; Cl, 13.32.

17. 2-(4-dimethylaminophenyl)imidazo[4,5-c]pyridine hydrochloride, orange crystals, m.p. about 296°–297° C.

Analysis: $C_{14}H_{15}ClN_4$; Calc: C, 61.20; H, 5.50; N, 20.39; Found: C, 60.19; H, 5.73; N, 19.98.

18. 2-(2-methoxyphenyl)imidazo[4,5-c]pyridine hydrochloride, tan needles, m.p. about 173°–175° C.

Analysis: $C_{13}H_{12}ClN_3O$; Calc: C, 59.66; H, 4.62; N, 16.06; Found: C, 59.32; H, 4.81; N, 16.10.

19. 2-(4-n-butoxyphenyl)imidazo[4,5-c]pyridine hydrochloride, light green needles, m.p. about 246°–248° C.

Analysis: $C_{16}H_{18}ClN_3O$; Calc: C, 63.26; H, 5.77; N, 13.83; Cl, 11.67; Found: C, 63.45; H, 5.98; N, 13.92; Cl, 11.93.

20. 2-(4-chloro-2-methoxyphenyl)imidazo[4,5-c]pyridine hydrochloride, light tan solid, m.p. about 227°–228° C.

Analysis: $C_{13}H_{11}ClN_3O$; Calc: C, 52.72; H, 3.74; N, 14.19; Cl, 23.94; Found: C, 52.56; H, 3.83; N, 13.98; Cl, 23.83.

21. 2-(3,5-dimethyl-4-methoxyphenyl)imidazo[4,5-c]pyridine hydrochloride, brown crystals, m.p. about 258°–259° C.

Analysis: $C_{15}H_{16}ClN_3O$; Calc: C, 62.18; H, 5.57; N, 14.50; Cl, 12.24; Found: C, 61.89; H, 5.52; N, 14.18; Cl, 11.98.

22. 2-(2,3,4-trimethoxyphenyl)imidazo[4,5-c]pyridine hydrochloride, cream colored solid, m.p. about 190° C.

Analysis: $C_{15}H_{16}ClN_3O_3$; Calc: C, 55.99; H, 5.01; N, 13.06; Cl, 11.02; Found: C, 55.75; H, 4.82; N, 12.94; Cl, 11.28.

23. 2-(2-methoxy-4-methylmercaptophenyl)imidazo[4,5-c]pyridine hydrochloride, bright yellow crystals, m.p. about 218°–221° C. (decomposition).

Analysis: $C_{14}H_{14}ClN_3OS$; Calc: C, 54.63; H, 4.58; N, 13.65; S, 10.42; Cl, 11.52; Found: C, 54.39; H, 4.42; N, 13.31; S, 10.22; Cl, 11.23.

EXAMPLE 24

2-(2,4-dimethylphenyl)imidazo[4,5-c]pyridine hydrochloride

Following the procedure of Example 1, 2,4-dimethylbenzoic acid and 3,4-diaminopyridine were reacted to give the title product as brown-green needles, m.p. about 295°–296° C.

Analysis: $C_{14}H_{14}ClN_3$; Calc: C, 64.74; H, 5.43; N, 16.18; Cl, 13.65; Found: C, 64.96; H, 5.27; N, 15.97; Cl, 13.69.

EXAMPLE 25

2-(4-methylphenyl)imidazo[4,5-c]pyridine hydrochloride

A mixture of 3,4-diaminopyridine (10 g., 92 mmoles), p-toluic acid (12.5 g., 92 mmoles) and 150 ml. of phosphorous pentoxide/methanesulfonic acid (1:10) was heated to 100°–120° C. for 3.5 hours. After cooling, the mixture was poured into 200 ml. of ice water. The resulting homogeneous solution was neutralized with 50% sodium hydroxide and the resulting precipitate was collected by filtration. The precipitate was flash chromatographed over silica gel eluting with 9:1 methylene chloride/methanol. The resulting product was crystallized from ethanol/water saturated with hydrogen chloride, and then recrystallized from ethanol/water, to give 5.0 g. (22% yield) of the title product as cream colored fluffy crystals, m.p. about 266°–267.5° C.

Analysis: $C_{13}H_{12}ClN_3$; Calc: C, 63.55; H, 4.92; N, 17.10; Cl, 14.43; Found: C, 63.40; H, 5.14; N, 16.83; Cl, 14.20.

EXAMPLE 26

2-(2-methylphenyl)imidazo[4,5-c]pyridine hydrochloride

Following the procedure of Example 25 using o-toluic acid, the title product was obtained as light tan needles, m.p. about 262.5°–263.5° C.

Analysis: $C_{13}H_{12}ClN_3$; Calc: C, 63.55; H, 4.92; N, 17.10; Cl, 14.43; Found: C, 63.25; H, 5.01; N, 16.71; Cl, 14.23.

EXAMPLE 27

2-(2-methoxy-4-methylsulfinylphenyl)imidazo[4,5-c]pyridine

A solution of 911 mg. (4.22 mmoles) of m-chloroperoxybenzoic acid in 50 ml. of chloroform was added in a dropwise fashion to a solution of 1.15 gm. (4.23 mmoles) 2-(2-methoxy-4-methylmercaptophenyl)imidazo[4,5-c]pyridine in 150 ml. of chloroform at 0° C. The reaction was stirred overnight at 0° C., washed with dilute aqueous sodium bicarbonate, and the solvent removed in vacuo. The residue was flash chromatographed over silica gel using dichloromethane/methanol (9:1) affording 620 mg. (51% yield) of the title product, m.p. about 143°–146° C. (decomposition).

Analysis: $C_{14}H_{13}N_3O_2S$; Calc: C, 58.52; H, 4.56; N, 14.62; S, 11.16; Found: C, 58.31; H, 4.72; N, 14.27; S, 11.03.

EXAMPLE 28–45

The following compounds were prepared from 3,4-diaminopyridine and the appropriate benzoic acid according to the procedure of Example 8.

28. 2-(2-ethoxy-4-methoxyphenyl)imidazo[4,5-c]pyridine, cream-colored crystals, m.p. about 157°–158° C.

Analysis: $C_{15}H_{15}N_3O_2$; Calc: C, 66.90; H, 5.61; N, 15.60; Found: C, 67.12; H, 5.53; N, 15.47.

29. 2-(2-n-propoxy-4-methoxyphenyl)imidazo[4,5-c]pyridine, cream-colored solid, m.p. about 125°–126° C.

Analysis: $C_{16}H_{17}N_3O_2$; Calc: C, 67.83; H, 6.05; N, 14.83; Found: C, 67.63; H, 5.74; N, 14.54.

30. 2-(2-n-butoxy-4-methoxyphenyl)imidazo[4,5-c]pyridine, cream-colored solid, m.p. about 123°–124° C.

Analysis: $C_{17}H_{19}N_3O_2$; Calc: C, 68.67; H, 6.44; N, 14.13; Found: C, 68.88; H, 6.54; N, 13.96.

31. 2-(2,5-dimethoxyphenyl)imidazo[4,5-c]pyridine hydrochloride, green solid, m.p. about 257°–259° C.

Analysis: $C_{14}H_{14}ClN_3O_2$; Calc: C, 57.64; H, 4.84; N, 14.40; Found: C, 55.51; H, 4.85; N, 13.70.

32. 2-(3,5-dimethoxyphenyl)imidazo[4,5-c]pyridine, tan solid, m.p. about 136°–139° C.

Analysis: $C_{14}H_{13}N_3O_2$; Calc: C, 65.87; H, 5.13; N, 16.46; Found: C, 66.17; H, 5.49; N, 16.22.

33. 2-(2,6-dimethoxyphenyl)imidazo[4,5-c]pyridine hydrochloride, tan solid, m.p. about 175°–177° C.

Analysis: $C_{14}H_{14}ClN_3O_2$; Calc: C, 57.64; H, 4.84; N, 14.40; Found: C, 48.44; H, 5.24; N, 11.67.

34. 2-(2,4,6-trimethoxyphenyl)imidazo[4,5-c]pyridine, red solid, m.p. about 132°–133° C.

Analysis: $C_{15}H_{15}N_3O_3$; Calc: C, 63.15; H, 5.30; N, 14.73; Found: C, 63.05; H, 5.58; N, 15.05.

35. 2-(2-n-pentoxy-4-methoxyphenyl)imidazo[4,5-c]pyridine hydrochloride, tan solid, m.p. about 188°–189° C.

Analysis: $C_{18}H_{22}ClN_3O_2$; Calc: C, 62.15; H, 6.38; N, 12.08; Found: C, 61.94; H, 6.51; N, 11.79.

36. 2-[2-(γ-methoxypropoxy)-4-methoxyphenyl]imidazo[4,5-c]pyridine, yellow crystals, m.p. about 123°–124.5° C.

Analysis: $C_{17}H_{19}N_3O_3$; Calc: C, 65.16; H, 6.11; N, 13.41; Found: C, 65.16; H, 5.99; N, 13.34.

37. 2-[2-(β-methoxyethoxy)-4-methoxyphenyl]imidazo[4,5-c]pyridine, yellow solid, m.p. about 137°–138.5° C.

Analysis: $C_{16}H_{17}N_3O_3$; Calc: C, 64.20; H, 5.72; N, 14.04; Found: C, 63.99; H, 5.47; N, 13.90.

38. 2-[2-(β-phenylmercaptoethoxy)-4-methoxyphenyl]imidazo[4,5-c]pyridine, yellow crystals, m.p. about 122°–123° C.

Analysis: $C_{21}H_{19}N_3O_2S$; Calc: C, 66.82; H, 5.07; N, 11.13; O, 8.48; S, 8.49; Found: C, 67.09; H, 5.33; N, 10.93; O, 8.61; S, 8.19.

39. 2-[2-(β-methylmercaptoethoxy)-4-methoxyphenyl]imidazo[4,5-c]pyridine, yellow crystals, m.p. about 140°–142.5° C.

Analysis: $C_{16}H_{17}N_3O_2S$; Calc: C, 60.93; H, 5.43; N, 13.32; S, 10.19; Found: C, 61.17; H, 5.45; N, 13.35; S, 9.96.

40. 2-(2,4,5-trimethoxyphenyl)imidazo[4,5-c]pyridine hydrochloride, yellow solid, m.p. about 247°–248° C. with decomposition.

Analysis: $C_{15}H_{16}ClN_3O_3$; Calc: C, 55.99; H, 5.01; N, 13.06; Cl, 11.02; Found: C, 55.65; H, 5.23; N, 12.77; Cl, 10.81.

41. 2-(2-methoxy-4-ethylmercaptophenyl)imidazo[4,5-c]pyridine hydrochloride, yellow solid, m.p. about 242°–243° C.

Analysis: $C_{15}H_{16}ClN_3OS$; Calc: C, 55.98; H, 5.01; N, 13.06; Found: C, 55.61; H, 4.82; N, 13.15.

42. 2-(2-ethoxy-4-methylmercaptophenyl)imidazo[4,5-c]pyridine, yellow crystals, m.p. about 136°–138° C.

Analysis: $C_{15}H_{15}N_3OS$; Calc: C, 63.13; H, 5.30; N, 14.73; Found: C, 63.35; H, 5.41; N, 14.86.

43. 2-(2-n-propoxy-4-methylmercaptophenyl)imidazo[4,5-c]pyridine, tan solid, m.p. about 144°–145° C.

Analysis: $C_{16}H_{17}N_3OS$; Calc: C, 64.19; H, 5.72; N, 14.04; Found: C, 64.26; H, 5.98; N, 13.80.

44. 2-[2-(γ-methylmercaptopropoxy)-4-methoxyphenyl]imidazo[4,5-c]pyridine, tan solid, m.p. about 105°–107° C.

Analysis: $C_{17}H_{19}N_3O_2S$; Calc: C, 61.98; H, 5.81; N, 12.76; O, 9.71; S, 9.73; Found: C, 61.89; H, 5.57; N, 12.59; O, 10.00; S, 9.46.

45. 2-[2-(β-ethylmercaptoethoxy)-4-methoxyphenyl]imidazo[4,5-c]pyridine hydrochloride, green solid, m.p. about 153°–156° C.

Analysis: $C_{17}H_{20}ClN_3O_2S$; Calc: C, 55.81; H, 5.51; N, 11.48; O, 8.75; S, 8.76; Cl, 9.69; Found: C, 55.55; H, 5.60; N, 11.28; O, 8.93; S, 9.05; Cl, 9.52.

EXAMPLES 46–49

The following compounds were prepared from 3,4-diaminopyridine and the appropriate benzoic acid derivative following the procedure of Example 1.

46. 2-(3,4-dimethylphenyl)imidazo[4,5-c]pyridine hydrochloride, tan solid, m.p. about 286°–287° C.

Analysis: $C_{14}H_{14}ClN_3$; Calc: C, 64.74; H, 5.43; N, 16.18; Cl, 13.65; Found: C, 64.52; H, 5.18; N, 15.89; Cl, 13.37.

47. 2-(2,4-dichlorophenyl)imidazo[4,5-c]pyridine, tan solid, m.p. about 179°–181° C.

Analysis: $C_{12}H_7Cl_2N_3$; Calc: C, 54.57; H, 2.67; N, 15.91; Found: C, 54.27; H, 2.93; N, 15.67.

48. 2-(3-chlorophenyl)imidazo[4,5-c]pyridine, tan solid, m.p. about 277°–279° C.

Analysis: $C_{12}H_8ClN_3$; Calc: C, 62.76; H, 3.51; N, 18.30; Found: C, 62.37; H, 3.71; N, 18.14.

49. 2-(4-chlorophenyl)imidazo[4,5-c]pyridine, tan solid, m.p. about 293°–295° C.

Analysis: $C_{12}H_8ClN_3$; Calc: C, 62.76; H, 3.51; N, 18.30; Found: C, 62.74; H, 3.44; N, 18.48.

EXAMPLE 50

2-(2-methoxy-4-methylsulfonylphenyl)imidazo[4,5-c]pyridine

A solution of 21.7 g. of sodium metaperiodate in 200 ml. of water was added to a solution of 25.0 g. of 2-(2-methoxy-4-methylmercaptophenyl)imidazo[4,5-c]pyridine in 750 ml. of methanol. After stirring at room temperature for about 2.5 hours, a solution of 16 g. of potassium permanganate in 200 ml. of water was added to the reaction mixture. The reaction was stirred for 30 minutes and then filtered. The filtrate was evaporated and the residue treated with boiling 50% chloroform/methanol for 30 minutes. The material was filtered and the filtrate was evaporated to dryness. The resulting solid was then triturated first with boiling methylene chloride, then with boiling water, and finally with boiling ethanol, to give 19.8 g. of the title product as a yellow powder, m.p. about 234°–235° C.

Analysis: $C_{14}H_{13}N_3O_3S$; Calc: C, 55.43; H, 4.32; N, 13.85; Found: C, 55.25; H, 4.51; N, 13.57.

EXAMPLE 51

2-(2-methoxy-4-methylsulfinylphenyl)imidazo[4,5-c]pyridine hydrochloride

Two grams of 2-(2-methoxy-4-methylmercaptophenyl)imidazo[4,5-c]pyridine were dissolved in 50 ml. of hot ethanol and then cooled. One hundred milliliters of chloroform were added and the solution was cooled to −30 to −40° C. by means of an external cooling bath. A solution of 1.455 g. of 85% meta-chloroperbenzoic acid in 10 ml. of chloroform was added to the solution over a one hour period. The solution was stirred for three additional hours at −30 to −40° C. The reaction was then warmed to room temperature and evaporated in vacuo. The resulting foam was dissolved in 20 ml. of dimethylformamide after which were added 1.3 ml. of concentrated hydrochloric acid. Diethyl ether was added to the cloud point and the solution was stirred for 30 minutes. The suspension was then chilled and filtered affording 2.1 g. of the title product as brown crystals, m.p. about 210°–212° C.

Analysis: $C_{14}H_{14}ClN_3O_2S$; Calc C, 51.93; H, 4.36; N, 12.98; Cl, 10.95; Found: C, 51.68; H, 4.54; N, 12.89; Cl, 11.05.

EXAMPLES 52–54

The following compounds were prepared from the corresponding mercapto derivatives according to the procedure of Example 27.

52. 2-[2-(β-methylsulfinylethoxy)-4-methoxyphenyl]imidazo[4,5-c]pyridine, light yellow crystals, m.p. about 195.5°–197° C.

Analysis: $C_{16}H_{17}N_3O_3S$; Calc: C, 57.99; H, 5.17; N, 12.68; S, 9.68; Found: C, 57.75; H, 4.99; N, 12.41; S, 9.45.

53. 2-[2-(β-phenylsulfinylethoxy)-4-methoxyphenyl]imidazo[4,5-c]pyridine, pale yellow solid, m.p. about 183°–184.5° C.

Analysis: $C_{21}H_{19}N_3O_3S$; Calc: C, 64.11; H, 4.87; N, 10.68; O, 12.20; S, 8.15; Found: C, 64.31; H, 4.66; N, 10.43; O, 12.05; S, 8.55.

54. 2-(2-n-propoxy-4-methylsulfinylphenyl)imidazo[4,5-c]pyridine, light yellow solid, m.p. about 98°–100° C.

Analysis: $C_{16}H_{17}N_3O_2S$; Calc: C, 60.93; H, 5.43; N, 13.32; Found: C, 60.34; H, 5.72; N, 12.21.

EXAMPLES 55–57

The following compounds were prepared from the appropriate benzoic acid and 3,4-diaminopyridine following the procedure of Example 8.

55. 2-(3-methoxy-4-methylmercaptophenyl)imidazo[4,5-c]pyridine hydrochloride, yellow solid, m.p. about 287°–288° C.

Analysis: $C_{14}H_{14}ClN_3OS$; Calc: C, 54.63; H, 4.58; N, 13.65; Found: C, 54.36; H, 4.31; N, 13.37.

56. 2-(3,4-dimethoxyphenyl)imidazo[4,5-c]pyridine hydrochloride, yellow crystals, m.p. about 263°–265° C.

Analysis: $C_{14}H_{14}ClN_3O_2$; Calc: C, 57.64; H, 4.84; N, 14.40; Found: C, 53.62; H, 4.86; N, 13.57.

57. 2-(2-methoxy-4-bromophenyl)imidazo[4,5-c]pyridine hydrochloride, tan solid, m.p. about 177°–182° C.

Analysis: $C_{13}H_{11}BrClN_3O$; Calc: C, 45.84; H, 3.26; N, 12.34; Found: C, 45.61; H, 3.29; N, 12.32.

EXAMPLE 58

2-(3-methoxy-4-methylsulfinylphenyl)imidazo[4,5-c]pyridine hydrochloride

The title compound was prepared from the corresponding mercapto derivative following the procedure of Example 27. The compound was a tan powder, m.p. about 252°–259° C. with decomposition.

Analysis: $C_{14}H_{14}ClN_3O_2S$; Calc: C, 51.93; H, 4.36; N, 12.98; Found: C, 51.78; H, 4.24; N, 12.67.

EXAMPLES 59–60

Following the general procedure of Example 8, the following compounds were prepared from 3,4-diaminopyridine and the appropriate benzoic acid.

59. 2-(2-Methoxy-4-trifluoromethylphenyl)imidazo[4,5-c]pyridine hydrochloride, white solid, m.p. about 210° C. with decomposition.

Analysis: $C_{14}H_{11}ClF_3N_3O$; Calc: C, 51.00; H, 3.36; N, 12.74; Cl, 10.75; Found: C, 50.75; H, 3.56; N, 12.45; Cl, 10.77.

60. 2-(2-Methoxy-4-nitrophenyl)imidazo[4,5-c]pyridine, yellow needles, m.p. about 220°–221.5° C.

Analysis: $C_{13}H_{10}N_4O_3$; Calc: C, 57.78; H, 3.73; N, 20.73; Found: C, 57.79; H, 3.73; N, 20.73.

The following formulation examples may employ as active compounds any of the pharmaceutical compounds of the invention.

EXAMPLE 61

Hard gelatin capsules are prepared using the following ingredients:

|  | Quantity (mg./capsule) |
|---|---|
| Active compound | 250 |
| Starch dried | 200 |
| Magnesium stearate | 10 |

The above ingredients are mixed and filled into hard gelatin capsules in 460 mg. quantities.

EXAMPLE 62

A tablet formula is prepared using the ingredients below:

|  | Quantity (mg./tablet) |
|---|---|
| Active compound | 250 |
| Cellulose, microcrystalline | 400 |
| Silicon dioxide, fumed | 10 |
| Stearic acid | 5 |

The components are blended and compressed to form tablets each weighing 665 mg.

EXAMPLE 63

An aerosol solution is prepared containing the following components:

|  | Weight % |
|---|---|
| Active ingredient | 0.25 |
| Ethanol | 29.75 |
| Propellant 22 (Chlorodifluoromethane) | 70 |

The active compound is mixed with ethanol and the mixture added to a portion of the propellant 22, cooled to −30° C. and transferred to a filling device. The required amount is then fed to a stainless steel container and diluted further with the remainder of the propellant. The valve units are then fitted to the container.

EXAMPLE 64

Tablets each containing 60 mg. of active ingredient are made up as follows:

| Active ingredient | 60 mg. |
|---|---|
| Starch | 45 mg. |
| Microcrystalline cellulose | 35 mg. |
| Polyvinylpyrrolidone (as 10% solution in water) | 4 mg. |
| Sodium carboxymethyl starch | 4.5 mg. |
| Magnesium stearate | 0.5 mg. |
| Talc | 1 mg. |
| Total | 150 mg. |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

EXAMPLE 65

Capsules each containing 80 mg. of medicament are made as follows:

| Active ingredient | 80 mg. |
|---|---|
| Starch | 59 mg. |
| Microcrystalline cellulose | 59 mg. |
| Magnesium stearate | 2 mg. |
| Total | 200 mg. |

The active ingredient, cellulose, starch and magnesium stearate are blended, passed through a No. 45 mesh U.S. sieve, and filled into hard gelatin capsules in 200 mg. quantities.

EXAMPLE 66

Suppositories each containing 225 mg. of active ingredient are made as follows:

| Active ingredient | 225 mg. |
|---|---|
| Saturated fatty acid glycerides to | 2,000 mg. |

The active ingredient is passed through a No. amesh U.S. sieve and suspended in the saturated fatty acid glycerides previously melted using the minimum heat necessary. The mixture is then poured into a suppository mold of nominal 2 g. capacity and allowed to cool.

EXAMPLE 67

Suspensions each containing 50 mg. of medicament per 5 ml. dose are made as follows:

| Active ingredient | 50 mg. |
|---|---|
| Sodium carboxymethyl cellulose | 50 mg. |
| Syrup | 1.25 ml. |
| Benzoic acid solution | 0.10 ml. |
| Flavor | q.v. |
| Color | q.v. |
| Purified water to | 5 ml. |

The medicament is passed through a No. 45 mesh U.S. sieve and mixed with the sodium carboxymethylcellulose and syrup to form a smooth paste. The benzoic acid solution, flavor and color are diluted with some of the water and added, with stirring. Sufficient water is then added to produce the required volume.

The compounds of this invention and their pharmaceutically acceptable salts have been found to possess useful pharmaceutical properties, including positive inotropy, vasodilation, and anticoagulation. Furthermore, these compounds may be useful in treating any condition characterized by excessive release of slow reacting substances of anaphylaxis (SRS-A), including immediate-type hypersensitivity reactions such as asthma. Certain compounds of the present invention were examined as to their pharmacodynamic effects in the following test systems.

Positive Inotropic Activity in Isolated Cat Papillary Muscles

Cats of either sex were anesthetized with Metofane (1,1-difluoro-2,2-dichloroethyl methyl ether, Pittman-Moore) their hearts immediately removed and the papillary muscles dissected and suspended in individual organ baths. A platinum hook secured one end of the muscle to an electrode mounted in the bottom of the bath, and a silk thread attached the tendon to a Statham isometric transducer. The baths contained Krebs-Henseleit solution (36° C., bubbled with 95 percent oxygen—5 percent carbon dioxide) of the following millimolar composition: NaCl, 118; KCl, 4.5; $CaCl_2$, 2.5; $KH_2PO_4$, 1.1; $MgSO_4$, 1.2; $NaHCO_3$, 25; and glucose, 11.

A base-line tension of 1.5 g. was applied to each muscle. Square-wave pulses (5.0 msec. in duration, three times threshold voltage) delivered through the hook electrode and a second electrode positioned near the top of the muscle evoked 12 contractions/minute, which were recorded on a Grass polygraph. After the muscles had equilibrated for 60 minutes, the recorder gain was adjusted so that the pen deflected 10 mm. The drug was introduced in a solution of normal saline in an amount to bring the final concentration of the drug to $10^{-5}$ or $10^{-4}$ molar. Increases in contractility were tabulated as millimeters of pen deflection in excess of the baseline value. In each experiment the maximum contractility was measured. Test results are summarized in Table I and are expressed as percent of control (control=100 percent). Values are the average of results from 2 to 8 muscles.

TABLE I

Effects of Imidazo[4,5-c]Pyridines on Contractility in Cat Papillary Muscles

| Compound of Example No. | Contractility of Papillary Muscle* Drug Concentration | |
|---|---|---|
| | $10^{-5}$ M | $10^{-4}$ M |
| 1 | 112 | 157 |
| 2 | 116 | 181 |
| 3 | 117 | 146 |
| 4 | 117 | 139 |
| 5 | 105 | 163 |
| 6 | 108 | 152 |
| 7 | 107 | 192 |
| 8 | 158 | 172 |
| 9 | 113 | 205 |
| 10 | 109 | 150 |
| 11 | 102 | 90 |
| 12 | 102 | 105 |
| 13 | 104 | 157 |
| 14 | 112 | 164 |
| 15 | 104 | 204 |
| 16 | 114 | 213 |
| 17 | 95 | 175 |
| 18 | 115 | 163 |
| 19 | 114 | 288 |
| 20 | 147 | 146 |
| 21 | 127 | 215 |
| 22 | 117 | 221 |
| 23 | 141 | 142 |
| 24 | 87 | 94 |
| 25 | 95 | 130 |
| 26 | 106 | 188 |
| 27 | 245 | 200 |
| 28 | 108 | 130 |
| 29 | 134 | 335 |
| 30 | 100 | 140 |
| 31 | 110 | 194 |
| 32 | 115 | 179 |
| 33 | 88 | 184 |
| 34 | 103 | 137 |
| 35 | 105 | 81 |
| 36 | 100 | 147 |
| 37 | 109 | 116 |
| 38 | 103 | 109 |
| 39 | 118 | 140 |
| 40 | 108 | 129 |
| 41 | 136 | 196 |
| 42 | 122 | 149 |
| 44 | 118 | 129 |
| 45 | 122 | 125 |
| 46 | 133 | 225 |
| 47 | 105 | 157 |
| 48 | 107 | 176 |
| 49 | 107 | 175 |
| 50 | 176 | 221 |
| 52 | 122 | 185 |
| 53 | 107 | 96 |
| 54 | 122 | 159 |
| 56 | 163 | 252 |
| 57 | 134 | 175 |
| 59 | 139 | 134 |
| 60 | 142 | 145 |

*Data are peak responses at the indicated concentration of drug and are expressed as a percent of control (control = 100 percent).

Experiments in Anesthetized Dogs

Mongrel dogs of either sex ranging in weight from 7 to 14 kg. wer used. Anesthesia was induced with sodium pentobarbital (30 mg./kg., i.v.) and maintained with supplemental doses as required. A positive-pressure pump was used to ventilate the dogs through an endotracheal tube (18 strokes/minute, 20 ml./kg. stroke$^{-1}$), and a heating pad kept the body temperature at 37°–38° C.

Femoral arterial blood pressure was measured through a polyethylene catheter filled with heparin solution (16 units/ml.) and connected to a Statham pressure transducer. A strain-gauge arch sutured to the right ventricle of the heart measured cardiac contractility. Tension on the gauge was adjusted to 50 g. and the gain of the recorder (Beckman dynograph) was set so that 50 g. caused a 10-mm. pen deflection; cardiac contractile tension was measured as millimeters of pen deflection or grams of tension. The drug was administered following a 30–45 minute equilibrium period as an i.v. bolus (2–5 ml.) in a normal saline vehicle. In a control experiment, rapid intravenous injection of 50 ml. of 5 percent dextran and mechanical compression of the aorta showed that the contractility measurements were independent of changes in preload and afterload. Heart rate was derived by means of a cardiotach which was triggered by the arterial pressure pulse signal and displayed on the polygraph. The maximum effects on contractility at various dose levels were determined and plotted and the dose required to produce a 50% increase in contractility ($ED_{50}$) was determined by interpolation. The $ED_{50}$'s for each compound tested are summarized in Table II.

TABLE II
Effects of Imidazo[4,5-c]Pyridines on Ventricular Contractility in the Anesthetized Dog

| Compound of Example No. | $ED_{50}$ (mg./kg.)* |
|---|---|
| 2 | 1.0 |
| 4 | 7.5 |
| 7** | 2.5 |
| 8 | 0.27 |
| 9 | 4.0 |
| 13 | 2.5 |
| 15 | 1.7 |
| 23 | 0.21 |
| 24 | 1.4 |
| 26 | 2.2 |
| 27 | 0.03 |
| 29 | 1.3 |
| 39 | 1.1 |
| 43 | 2.2 |
| 45 | 1.0 |
| 47 | 0.67 |
| 50 | 0.02 |
| 52 | 5.2 |
| 54 | 1.0 |
| 56 | 0.38 |
| 59 | 0.005 |
| 60 | 0.015 |

*i.v. dose required to produce a peak increase in contractility of 50%.
**tested as the hydrochloride salt.

Inhibition of SRS-A (Slow-Reacting Substance of Anaphylaxis) From Guinea Pig Lung Male, Hartley guinea pigs, usually 1–2 weeks old, were sensitized with respect to ovalbumin by intraperitoneal administration of 0.15 ml. hyperimmune serum obtained from guinea pigs actively sensitized against ovalbumin. After 2 days or more, the animals were decapitated, lungs were excised and perfused through the pulmonary artery with Krebs' bicarbonate solution of the following composition in mmoles/liter: KCl, 4.6; $CaCl_2.2H_2O$, 1.8; $KH_2PO_4$, 1.2; $MgSO_4.7H_2O$, 1.2; NaCl, 118.2; $NaHCO_3$, 24.8; and dextrose, 10.0. Poorly perfused and bloody areas were discarded. Normal lung was cut into 1 mm. cubes with a McIlwain tissue chopper, washed with Krebs' solution and divided into 400 mg. aliquots. The fragmented tissue was then incubated at 37° C. for 15 minutes in Krebs' solution containing indomethacin to optimize SRS-A release and an appropriate concentration of experimental drug. Antigen (ovalbumin) was then added to make a final concentration of $1 \times 10^{-5}$ g./ml. Fifteen minutes later, the incubation medium was decanted and centrifuged at $3,000 \times g$ at 4° C. for 5 minutes. The supernatant solution was collected and assayed for SRS-A using a computerized bioassay that employs the isolated guinea pig ileum (Fleisch et al., *J. Pharmacol. Exp. Ther.*, 209, 238–243, 1979). Release of SRS-A in the presence of the experimental drug was compared to a control sample and the results expressed as percent inhibition of SRS-A release. 2-(2,4-dimethoxyphenyl)imidazo[4,5-c]pyridine hydrochloride inhibited SRS-A release 19.4% at $1 \times 10^{-5}$M and 45.1% at $1 \times 10^{-4}$M.

We claim:

1. A method of producing a positive inotropic effect, delaying coagulation of the blood, causing bronchodilation, or causing vasodilation in a mammal, which comprises the administration to such mammal an effective amount of a compound of the formula

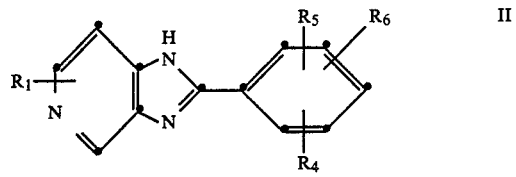

or

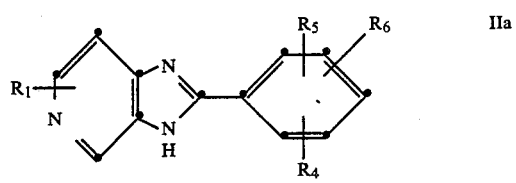

or its pharmaceutically acceptable salt, wherein
$R_1$ is hydrogen, $C_1$–$C_4$ alkyl, or chloro;
$R_4$ is hydrogen, $C_1$–$C_4$ alkyl, or $C_1$–$C_4$ alkoxy; and
each of $R_5$ and $R_6$ is independently hydrogen, $C_1$–$C_4$ alkyl, $C_1$–$C_4$ alkoxy, allyloxy, $C_1$–$C_4$ alkylthio, $C_1$–$C_4$ alkylsulfinyl, $C_1$–$C_4$ alkylsulfonyl, hydroxy, halo, cyano, nitro, amino, mono- or di-($C_1$–$C_4$ alkyl)amino, trifluoromethyl, or Z-Q-substituted $C_1$–$C_4$ alkoxy, wherein Q is oxygen, sulfur, sulfinyl, sulfonyl, or a bond, and Z is $C_1$–$C_4$ alkyl, phenyl, or phenyl substituted with halo, $C_1$–$C_4$ alkyl, $C_1$–$C_4$ alkoxy, hydroxy, nitro, amino, $C_1$–$C_4$ alkylthio, $C_1$–$C_4$ alkylsulfinyl, or $C_1$–$C_4$ alkylsulfonyl.

2. The method of claim 1 wherein the compound is 2-(2-methoxy-4-methylsulfinylphenyl)imidazo[4,5-c]pyridine or a pharmaceutically acceptable salt thereof.

3. The method of claim 1 wherein the compound is 2-(2-methoxy-4-methylsulfonylphenyl)imidazo[4,5- c]pyridine or a pharmaceutically acceptable salt thereof.

4. The method of claim 1 wherein the compound is 2-(2-methyoxy-4-trifluoromethylphenyl)imidazo[4,5-c]pyridine or a pharmaceutically acceptable salt thereof.

5. A pharmaceutical composition useful for producing an inotropic effect in mammals which comprises a pharmaceutically acceptable carrier or diluent and an effective amount of a compound of the formula

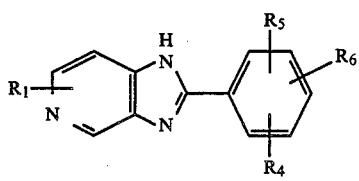

or

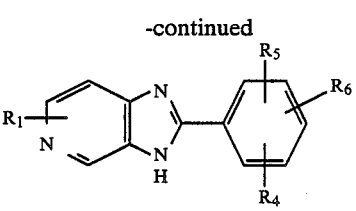

or its pharmaceutically acceptable salt, wherein
$R_1$ is hydrogen, $C_1$-$C_4$ alkyl, or chloro;
$R_4$ is hydrogen, $C_1$-$C_4$ alkyl, or $C_1$-$C_4$ alkoxy; and
each of $R_5$ and $R_6$ is independently hydrogen, $C_1$-$C_4$ alkyl, $C_1$-$C_4$ alkoxy, allyloxy, $C_1$-$C_4$ alkylthio, $C_1$-$C_4$ alkylsulfinyl, $C_1$-$C_4$ alkylsulfonyl, hydroxy, halo, cyano, nitro, mono- or di-($C_1$-$C_4$ alkyl)-amino, trifluoromethyl, or Z-Q-substituted $C_1$-$C_4$ alkoxy, wherein Q is oxygen, sulfur, sulfinyl, sulfonyl, or a bond, and Z is $C_1$-$C_4$ alkyl, phenyl, or phenyl substituted with halo, $C_1$-$C_4$ alkyl, $C_1$-$C_4$ alkoxy, hydroxy, nitro, amino $C_1$-$C_4$ alkylsulfonyl.

6. The composition of claim 5 wherein the compound is 2-(2-methoxy-4-methylsulfinylphenyl)imidazo[4,5-c]pyridine or a pharmaceutically acceptable salt thereof.

7. The composition of claim 5 wherein the compound is 2-(2-methoxy-4-methylsulfonylphenyl)imidazo[4,5-c]pyridine or a pharmaceutically acceptable salt thereof.

8. The composition of claim 5 wherein the compound is 2-(2-methoxy-4-trifluoromethylphenyl)imidazo[4,5-c]pyridine or a pharmaceutically acceptable salt thereof.

* * * * *

UNITED STATES PATENT AND TRADEMARK OFFICE
CERTIFICATE OF CORRECTION

PATENT NO. : 4,758,574

DATED : July 19, 1988

INVENTOR(S) : David W. Robertson & J. Scott Hayes

It is certified that error appears in the above-identified patent and that said Letters Patent is hereby corrected as shown below:

Column 10, Line 29, "(1.09 g., 1 mmoles)," should read --(1.09 g., 10 mmoles),--.

Column 19, Line 13, "No. αmesh" should read --No. 60 mesh--.

On the title page, item [54] and column 1, the title of invention, "2-PHENYLIMIDAZIO" should read --2-PHENYLIMIDAZO--.

Signed and Sealed this

Twenty-eighth Day of November 1989

Attest:

JEFFREY M. SAMUELS

Attesting Officer     Acting Commissioner of Patents and Trademarks

Disclaimer 4,758,574—*David W. Robertson, J. Scott Hayes*, both of Indianapolis, Ind. 2-PHENYLIMIDAZO (4,5-C) PYRIDINES. Patent dated July 19, 1988. Disclaimer filed May 13, 1991, by the assignee, Eli Lilly and Co.

Hereby enters this disclaimer to all claims of said patent.
[ *Official Gazette July 16, 1991* ]